(12) United States Patent
Butler et al.

(10) Patent No.: US 6,313,285 B1
(45) Date of Patent: Nov. 6, 2001

(54) PURIFICATION OF PLASMID DNA

(75) Inventors: Michelle D. Butler, San Francisco; Darien L. Cohen, Oakland; David Kahn, Foster City; Marjorie E. Winkler, Burlingame, all of CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 09/620,849

(22) Filed: Jul. 21, 2000

Related U.S. Application Data

(60) Provisional application No. 60/165,206, filed on Nov. 12, 1999, and provisional application No. 60/145,316, filed on Jul. 23, 1999.

(51) Int. Cl.$^7$ .................................................. C12N 15/10
(52) U.S. Cl. ...................................... 536/25.4; 435/320.1
(58) Field of Search ......................... 435/320.1; 536/25.4

(56) References Cited

U.S. PATENT DOCUMENTS

| | | | |
|---|---|---|---|
| 4,673,642 | * 6/1987 | Puhler et al. | 435/91.1 |
| 5,256,294 | 10/1993 | Van Reis | 210/637 |
| 5,490,937 | 2/1996 | Van Reis | 210/637 |
| 5,707,812 | 1/1998 | Horn et al. | 435/6 |
| 6,011,148 | 1/2000 | Bussey et al. | 536/25.4 |

FOREIGN PATENT DOCUMENTS

| | | |
|---|---|---|
| 307373 | 3/1989 | (EP) . |
| 853123 | 7/1998 | (EP) . |
| WO 87/04169 | 7/1987 | (WO) . |
| WO 96/02658 | 2/1996 | (WO) . |
| WO 98/05673 | 2/1998 | (WO) . |
| WO 99/11764 | 3/1999 | (WO) . |
| WO 99/16869 | 4/1999 | (WO) . |
| WO 99/63076 | 12/1999 | (WO) . |
| WO 00/09680 | 2/2000 | (WO) . |

OTHER PUBLICATIONS

J. Sambrook et al. Molecular Cloning A laboratory Manual second edition 1989 Cold Spring Harbor Laboratory Press VII–VIII, 1.36–1.37,1.42–1. 46.*

Birnboim and Doly, "A Rapid Alkaline Extraction Procedure for Screening Recombinant Plasmid DNA" *Nucleic Acids Research* 7(6):1513–1523 (1979).

Chakrabarti et al., "A Proceudre for Large–Scale Plasmid Isolation without Using Ultracentrifugation" *Biotech. Appl. Biochem.* 16:211–215 (1992).

Chandra et al., "Large–Scale Purification of Plasmid DNA by Fast Protein Liquid Chromatography Using a Hi–Load Q Sepharose Column" *Analytical Biochemistry* 203:169–172 (1992).

Clewell and Helinski, "Supercoiled Circular DNA–Protein Complex in *Escherichia coli*: Purification and Induced Conversion to an Open Circular DNA Form" *Proc. Natl. Acad. Sci. USA* 62:1159–1166 (1969).

Cole, K., "Purification of Plasmid and High Molecular Mass DNA Using PEG–Salt Two–Phase Extraction" *BioTechniques* 11(1):18–24 (1991).

Colman et al., "Rapid Purification of Plasmid DNAs by Hydroxyapatite Chromatography" *European Journal of Biochemistry* 91:303–310 (1978).

Cornelis et al., "Purification of *Escherichia coli* Amplifiable Plasmids by High–Salt Sepharose Chromatography" *Plasmid* 5:221–223 (1981).

Cotten et al., "Lipopolysaccharide is a frequent contaminant of plasmid DNA preparations and can be toxic to primary human cells in the presence of adenovirus" *Gene Ther.* 1:239–246 (1994).

Edwardson et al., "A New Rapid Procedure for the Preparation of Plasmid DNA" *Analytical Biochemistry* 152:215–220 (1986).

Flanagan et al., "Nucleic Acid Chromatography: Substitute Solid Support Material for RPC–5 Columns" *Analytical Biochemistry* 153:299–304 (1986).

Gabler, "Tangential flow filtration for processing cells, proteins, and other biological components" *ASM News* 50(7):299–304 (1984).

Garon and Peterson, "An Improved Method for the Isolation of Supercoiled DNA Molecules Using Ion–Exchange Column Chromatography" *Gene Anal. Tech.* 4:5–8 (1987).

Hansen and Rickett, "Large–Scale Purification of Plasmid Insert DNA Sequences Using Low–Percentage Agarose Exclusion Chromatography" *Analytical Biochemistry* 179:167–170 (1989).

Hill et al., "The same prion strain causes vCJD and BSE" *Nature* 389:448–450 (1997).

Holmes and Quigley, "A Rapid Boiling Method for the Preparation of Bacterial Plasmids" *Analytical Biochemistry* 114:193–197 (1981).

Horn et al., "Cancer Gene Therapy Using Plasmid DNA: Purification of DNA for Human Clinical Trials" *Human Gene Ther.* 6:565–573 (1995).

Ishaq et al., "Large Scale Isolation of Plasmid DNA Using Cetyltrimethylammonium Bromide" *Biotechniques* 9:19–24 (1990).

(List continued on next page.)

*Primary Examiner*—James Ketter
*Assistant Examiner*—Lisa Gansheroff
(74) *Attorney, Agent, or Firm*—Janet E. Hasak

(57) ABSTRACT

A process is described for purifying plasmid DNA from prokaryotic cells comprised thereof. This process comprises the steps of: (a) digesting the cells; (b) incubating the cells for about 4 to 24 hours to effect lysis and solubilization thereof, without effecting enzymatic digestion of RNA; (c) removing lysate contaminants from the cells to provide a plasmid DNA solution; (d) filtering the solution through a tangential flow filtration device to obtain a retentate containing the plasmid DNA; and (e) collecting the retentate.

15 Claims, 1 Drawing Sheet

OTHER PUBLICATIONS

Johnson and Ilan, "Large–Scale Isolation of Plasmid DNA and Purification of λ Phage DNA Using Hydroxylapatite Chromatography" *Analytical Biochemistry* 132:20–25 (1983).

Johnson et al., "A Convenient, New Method for Desalting, Deproteinizing, and Concentrating DNA or RNA" *Biotechniques* 4:64–70 (1986).

Kim and Rha, "Selective Adsorption/Desorption of Nucleic Acids on Submicron–Sized Polymeric Particles" *Biotech. Bioeng.* 33:1205–1209 (1989).

Kondo et al., "Rapid Isolation of Plasmid DNA by LiCl–Ethidium Bromide Treatment and Gel Filtration" *Analytical Biochemistry* 198:30–35 (1991).

Lis and Schleif, "Size fractionation of double–stranded DNA by precipitation with polyethylene glycol" *Nucleic Acids Research* 2:383–389 (1975).

Marko et al., "A Procedure for the Large–Scale Isolation of Highly Purified Plasmid DNA Using Alkaline Extraction and Binding to Glass Powder" *Analytical Biochemistry* 121:382–387 (1982).

Marquet et al., "Process Development for the Manufacture of Plasmid DNA Vectors for Use in Gene Therapy" *BioPharm.* pp. 26–37 (1995).

Matsushita et al., "Cross–flow Filtration of Yeast Extract with Multi–Tubular Membrane Module and Rotating–disk Membrane Module" *Kagaku Kogaku Ronbunshu* 20:725–728 (1994).

McClung and Gonzales, "Purification of Plasmid DNA by Fast Protein Liquid Chromatography on Superose 6 Preparative Grade" *Analytical Biochemistry* 177:378–382 (1989).

Micard et al., "Purification of RNA–Free Plasmid DNA Using Alkaline Extraction followed by Ultrogel A2 Column Chromatography" *Analytical Biochemistry* 148:121–126 (1985).

Michaels et al., "Tangential Flow Filtration" *Separations Technology, Pharmaceutical and Biotechnology Applications*, W. P. Olson, Buffalo Grove, IL:Interpharm Press, Inc. (1995), pp. 57–194.

Moreau et al., "Purification and Separation of Various Plasmid Forms by Exclusion Chromatography" *Analytical Biochemistry* 166:188–193 (1987).

Ohmiya et al., "Separation of DNA Fragments by High–Resolution Ion–Exchange Chromatography on a Nonporous QA Column" *Analytical Biochemistry* 189:126–130 (1990).

Perbal et al. *A Practical Guide to Molecular Cloning*, New York:Wiley pp. 165–175 (1984).

Raymond et al., "Large–Scale Isolation of Covalently Closed Circular DNA Using Gel Filtration Chromatography" *analytical Biochemistry* 173:125–133 (1988).

Richards and Goldmintz, "Evaluation of a Cross–Flow Filtration Technique for Extraction of Polioviruses from Inoculated Oyster Tissue Homogenates" *J. Virol. Methods* 4:147–153 (1982).

Roman and Brown, "Separation techniques for biotechnology in the 1990s" *J. Chromatogr.* 592:3–12 (1992).

Ruppert et al., "A Filtration Method for Plasmid Isolation Using Microtiter Filter Plates" *Analytical Biochemistry* 230:130–134 (1995).

Sambrook et al. *Molecular Cloning: A Laboratory Manual*, 2 edition, New York: Cold Spring Harbor Laboratory Press pp. 1.21–1.52 (1989).

Sekhar et al., "Retroviral Transduction of CD34–Enriched Hematopoietic Progenitor Cells Under Serum–Free Conditions" *Human Gene Therapy* 7:33–38 (1996).

van Helden and Hoal, "Plasmid Preparation on Sephacryl S1000" *New Nucleic Acid Techniques*, Walker, Clifton, NJ: Humana Press, Chapter 7, pp. 69–74 (1988).

van Huynh et al., "Sequential Elution of Denatured Proteins, Hydrolyzed RNA, and Plasmid DNA of Bacterial Lysates Adsorbed onto Stacked DEAE–Cellulose Membranes" *Analytical Biochemistry* 211:61–65 (1993).

Vincent and Goldstein, "Rapid Preparation of Covalently Closed Circular DNA by Acridine Yellow Affinity Chromatography" *Analytical Biochemistry* 110:123–127 (1981).

Weber et al., "Effects of Lipopolysaccharide on Transfection Efficiency in Eukaryotic Cells" *Biotechniques* 19:930–940 (1995).

Zasloff et al., "A new method for the purification and identification of covalently closed circular DNA molecules" *Nucleic Acids Research* 5:1139–1153 (1978).

Fernandez et al., "Cross Flow Filtration of RNA Extracts by Hollow Fiber Membrane" *Acta Biotechnologica* 12(1):49–56 (1992).

Kahn et al., "Purification of Plasmid DNA by Tangential Flow Filtration" *Biotechnology and Bioengineering* 69(1):101–106 (2000).

Rembhotkar and Khatri, "Large Scale Preparation of Bacteriophage λ by Tangential Flow Ultrafiltration for Isolation of λ DNA" *Analytical Biochemistry* 176(2):373–374 (1989).

\* cited by examiner

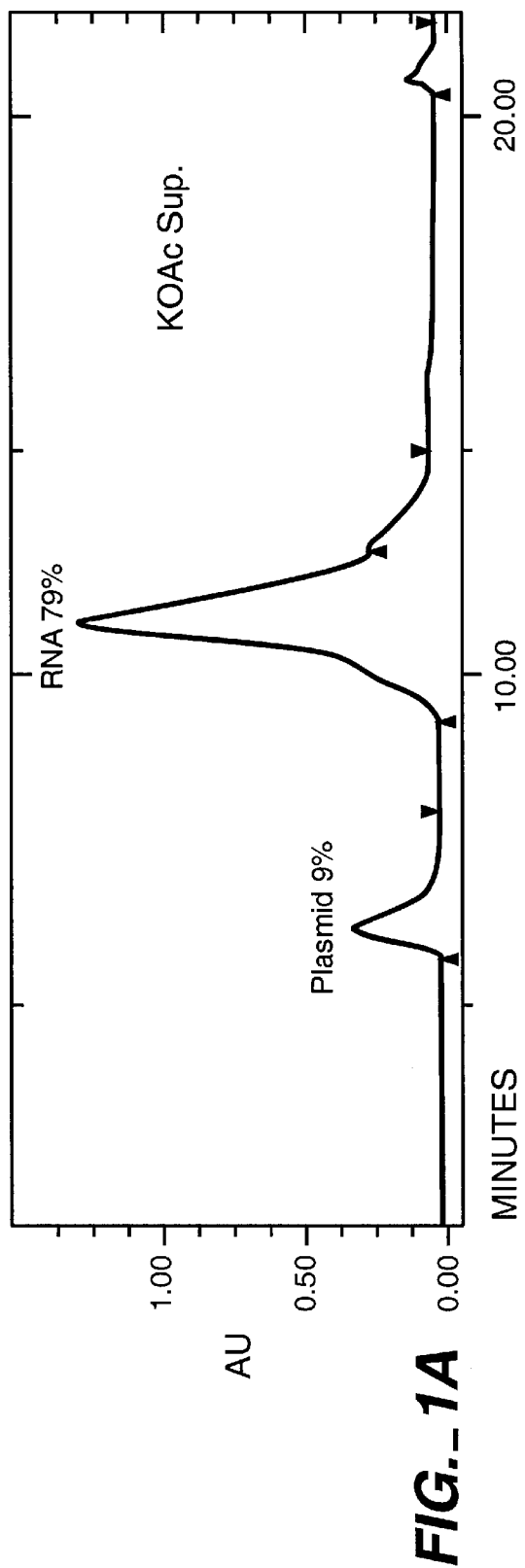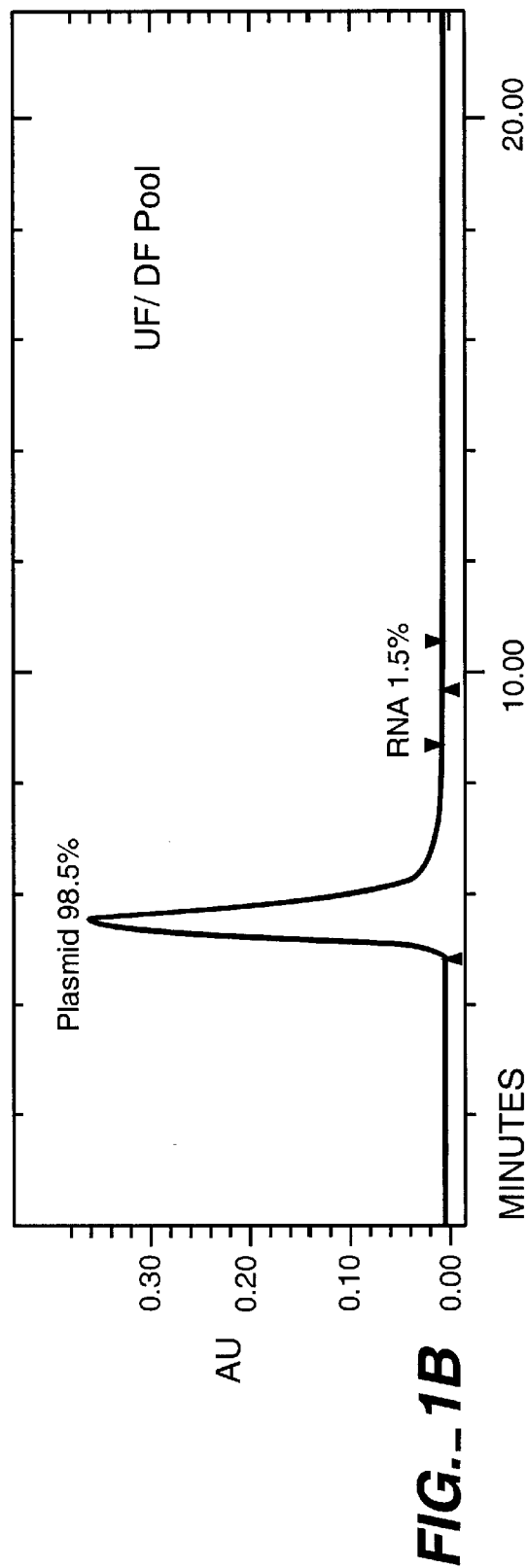

PURIFICATION OF PLASMID DNA

RELATED APPLICATIONS

This application is a non-provisional application filed under 37 CFR 1.53(b) (1), claiming priority under 35 USC 119(e) to provisional application No. 60/145,316 filed Jul. 23, 1999, and 60/165,206 filed Nov. 12, 1999, the contents of which are incorporated herein by reference.

BACKGROUND OF THE INVENTION

1. Field of the Invention

The present invention relates to a process for purification of plasmid DNA. More specifically, a method is provided that is simple and scalable and utilizes tangential flow filtration, resulting in higher yields of highly pure plasmid than the classical alkaline-lysis-based method.

2. Description of Related Disclosures

Purification of plasmid DNA from cell cultures is a prerequisite for many studies and pharmaceutical uses. In general, plasmid purification methods may be considered as two-stage processes involving an initial cell disruption/plasmid isolation step followed by one or more subsequent purification steps. The most common methods for initial isolation are modified versions of two approaches: one based on release of plasmid by boiling (Holmes and Quigley, *Anal. Biochem.*, 114: 193–197 (1981)) and the second based on alkaline pH and detergent-mediated solubilization of the bacterial cell membranes (Birnboim and Doly, *Nucleic Acids Res.*, 7: 1513–1523 (1979)). Both of these methods result in the release of plasmid DNA from its cytosolic location.

In addition to the common use of ultracentrifugation through cesium chloride gradients (Clewell and Helinski, *Proc. Natl. Acad. Sci. USA*, 62: 1159–1166 (1969)), downstream purification has typically involved either selective precipitation of plasmid from contaminants (Lis and Schleif, *Nucleic Acids Res.*, 2: 383–389 (1975); Ishaq et al., *Biotechniques*, 9: 19–24 (1990); Kondo et al., *Anal. Biochem.*, 198: 30–35 (1991); Chakrabarti et al., *Biotech. Appl. Biochem.*, 16: 211–215 (1992)) and/or the use of column chromatography (Horn et al., *Human Gene Ther.*, 6: 565–573 (1995); U.S. Pat. No. 5,707,812; Chandra et al., *Anal. Biochem.*, 203: 169–172 (1992); Marquet et al., *BioPharm*: 26–37 (1995); Johnson and Ilan, *Anal. Biochem.*, 132: 20–25 (1983); Vincent and Goldstein, *Anal. Biochem.*, 110: 123–127 (1981)). Column chromatography protocols rely on reverse-phase (Edwardson et al., *Anal. Biochem.*, 152: 215–220 (1986); Johnson et al., *Biotechniques*, 4: 64–70 (1986); van Helden and Hoal in *New Nucleic Acid TechniQues*, Walker, Ed. (Humana Press: Clifton, N.J. 1988), pp. 69–74)), normal-phase (Marko et al., *Anal. Biochem.*, 121: 382–387 (1982)), ion-exchange (Perbal in A *Practical Guide to Molecular Cloning* (Wiley: New York, 1984), pp. 165–175; Colman et al., *Eur. J. Biochem.*, 91: 303–310 (1978); Garon and Petersen, *Gene Anal. Tech.*, 4: 5–8 (1987); Kim and Rha, *Biotech. Bioeng.*, 33: 1205–1209 (1989); Ohmiya et al., *Anal. Biochem.*, 189: 126–130 (1990)), size-exclusion (van Helden and Hoal, supra; Perbal, supra; Cornelis et al., *Plasmid*, 5: 221–223 (1981), Micard et al., *Anal. Biochem.*, 148: 121–126 (1985); Moreau et al., *Anal. Biochem.*, 166: 188–193 (1987); Raymond et al., *Anal. Biochem.*, 173: 125–133 (1988); Hansen and Rickett, *Anal. Biochem.*, 179: 167–170 (1989)), and mixed-mode (Flanagan et al., *Anal. Biochem.*, 153: 299–304 (1986)) methodologies.

Alternatives to these approaches include the use of 0.2-micron membranes as a substitute for a centrifugation step during alkaline lysis in a 96-well plate format (Ruppert et al., *Anal. Biochem.*, 230: 130–134 (1995)), the use of aqueous two-phase separation (Cole, *Biotechniques*, 11: 18–24 (1991)), and the use of ion-exchange membranes (van Huynh et al., *Anal. Biochem.*, 211: 61–65 (1993)) for plasmid purification. Typically, these methods have required additional purification steps involving either organic solvent-based extraction (e.g., phenol/chloroform) or precipitation (e.g., isopropanol, ethanol) steps, as well as the addition of exogenous enzymes (e.g., RNase, Proteinase K) to produce plasmid of adequate purity.

Additional techniques for plasmid DNA purification involve polyethylene-glycol-based DNA purification methods (Lis and Schleif, supra; U.S. Pat. No. 5,707,812 wherein a short-chain polymeric alcohol is added to the lysate so that the lysate will bind to the column or membrane used for purification); acid-phenol purification of plasmid DNA (Zasloff et al., *Nucleic Acids Res.*, 5: 1139–1153 (1978)); and different methods for relatively small-scale purification of plasmid DNA for research use (Sambrook et al., *Molecular Cloning: A Laboratory Manual*, $2^{nd}$ ed. (Cold Spring Harbor Laboratory Press: New York, 1989); Ausubel et al., eds., *Current Protocols in Molecular Biolocy*, (John Wiley & Sons: New York, 1989)). Techniques for DNA-RNA separations are reviewed in Roman and Brown, *J. Chromatogr.*, 592: 3–12 (1992).

Tangential flow filtration (TFF), or cross-flow filtration, is a separation technique whereby flow is directed across the membrane surface in a sweeping motion (Gabler, *ASM News*, 50: 299 (1984)). This sweeping action helps to keep material retained by the membrane from creating a layer on the filter surface, a condition known as concentration polarization. TFF is used to concentrate and/or desalt solutions retained by the membrane (retentate) or to collect material passing through the membrane (filtrate). Materials smaller than the pore size (or nominal-molecular-weight cutoff (NMWC)) are able to pass through the membrane and may be depyrogenated, clarified, or separated from higher-molecular-weight or larger species. Materials larger than the pore size or NMWC are retained by the membrane and are concentrated, washed, or separated from the low-molecular-weight species. The principles, theory, and devices used for TFF are described in Michaels et al., "Tangential Flow Filtration" in *Separations Technology, Pharmaceutical and Biotechnology Applications* (W. P. Olson, ed., Interpharm Press, Inc., Buffalo Grove, Ill. 1995). See also U.S. Pat. Nos. 5,256,294 and 5,490,937 for a description of high-performance tangential flow filtration (HP-TFF), which represents an improvement to TFF; and WO 87/04169 for a description of tangential flow affinity ultrafiltration, which involves mixing the solution to be purified with an affinity gel that selectively binds to the substance to be purified and then subjecting the liquid to TFF so that all components except the bonded material pass through the filter.

Additional methods for purification of viruses, nucleic acid, bacteriophage, and other biological materials using physical separation such as TFF or other cross-flow filtration techniques are set forth in various publications (Richards and Goldmintz, *J. Virol. Methods*, 4: 147–153 (1982); Fernandez et al., *Acta Biotechnol.*, 12: 49–56 (1992); Matsushita et al., *Kagaku Kogaku Ronbunshu*, 20: 725–728 (1994); Rembhotkar and Khatri, *Anal. Biochem.*, 176:373–374 (1989); WO 98/05673 published Feb. 12, 1998; EP 307,373; Sekhar et al., *Hum. Gene Ther.*, 7: 33–38 (1996)).

With the increasing utilization of plasmid DNA as biopharmaceuticals in gene therapy applications rather than as a cloning vector, a growing need exists for simple, robust, and scalable purification processes that can be used in the isolation of both intermediate and large amounts of this molecule from transformed prokaryotes. The use of plasmid purification methods that are currently available for the purpose of generating large amounts of research material, or for supplying a clinical trial, is limited for many reasons. Purification schemes that involve the use of large amounts of flammable organic solvents (e.g., ethanol and isopropanol), toxic chemicals (e.g., ethidium bromide, phenol, and chloroform). Ultracentrifuges and "spin-columns," while adequate for the generation of small amounts of research material, are not suitable for use in generating the quantities of material needed for biopharmaceutical applications.

In addition, many current plasmid purification procedures involve the addition of RNase, typically from bovine origin. Materials derived from bovine sources are increasingly undesirable in the manufacture of pharmaceuticals due to concerns regarding bovine spongiform encephalopathies (BSE) (Hill et al., Nature, 389: 448–450 (1997)). In general, it is desirable to avoid the addition of enzymes to plasmid preparations, as these molecules must subsequently be purified away.

Purification protocols involving the use of gel-filtration chromatography are hampered by the low load capacities inherent in the operation; in one report, loads were limited to approximately two percent of the volume of the column (McClung and Gonzales, Anal. Biochem., 177: 378–382 (1989)).

SUMMARY OF THE INVENTION

Accordingly, the present invention provides a process for purifying plasmid DNA from prokaryotic cells comprised thereof, which process comprises the steps of:

(a) digesting the cells;

(b) incubating the cells for about 4 to 24 hours to effect lysis and solubilization thereof, without effecting enzymatic digestion of RNA;

(c) removing lysate contaminants from the cells to provide a plasmid DNA solution;

(d) filtering the solution through a tangential flow filtration device to obtain a retentate containing the plasmid DNA; and (e) collecting the retentate.

The cells are preferably bacterial cells. Also preferred is that step (c) be carried out by centrifuging the lysate contaminants from the plasmid DNA in the cell lysate to provide a supernatant solution comprising the plasmid DNA.

In another embodiment, the invention provides a composition comprising plasmid DNA prepared according to the above process.

A simple, scalable, filtration-based method for purification of plasmid DNA is provided herein that results in the production of high-purity plasmid at very high yield. This method includes modification of the classical alkaline-lysis-based plasmid extraction method by extending the solubilization step from less than 30 minutes to from about 4 to 24 hours. The extraction is followed by the novel use of TFF for purification of the remaining contaminants. The method herein does not involve the use of any organic solvents, RNase, Proteinase K, high-speed centrifugation, or column chromatography steps. The use of organic solvents poses safety and regulatory concerns in that it might leave trace amounts in the final product; also such solvents are toxic and inflammable, posing serious risk and disposal/environmental problems when used in the amounts required for large-scale purification. The method typically yields 15–20 mg of plasmid DNA per liter of bacterial culture and results in removal of greater than 99% of RNA and greater than 95% of the protein that remains after the modified alkaline lysis procedure. Plasmid isolated using this procedure had comparable transfection capability compared to plasmid isolated using a classical cesium chloride gradient-based method.

Since the plasmid DNA herein is purified to a high degree, it can be beneficially used for gene therapy and other gene delivery techniques, for example, those involving lipid carriers, whereby reproducible, high-transfection efficiencies are obtained. The method described is readily scaled up for operation at larger capacity, as required.

BRIEF DESCRIPTION OF THE DRAWINGS

FIGS. 1A and 1B show the purification of plasmid DNA from RNA as assessed by size-exclusion chromatography. FIG. 1A is an analysis of the potassium acetate supernatant prior to purification by TFF. FIG. 1B depicts the analysis of the final TFF pool. Values indicate the percent of total absorbance at 260 nm.

DETAILED DESCRIPTION OF THE PREFERRED EMBODIMENTS

Definitions:

As used herein, "filtrate" refers to that portion of a sample that passes through the filtration membrane.

As used herein, "retentate" refers to that portion of a sample that does not pass through the filtration membrane.

"Tangential flow filtration" or "TFF" or "crossflow filtration" refers to a filtration process in which the sample mixture circulates across the top of the membrane, while applied pressure causes solute and small molecules to pass through the membrane. Typically, the solution flows parallel to the filter membrane so that the fluid flow continually cleans the filter surface and prevents clogging by nonfilterable solutes. A pressure differential across the membrane causes fluid and filterable solutes to flow through the filter. This can be conducted as a continuous-flow process, since the solution is passed repeatedly over the membrane while that fluid that passes through the filter is continually drawn off into a separate circuit.

As used herein, "lysate contaminants" refers to all undesired components of a mixture in which the desired plasmid DNA is contained, including chromosomal DNA, host proteins, cell debris, including cell membrane debris, carbohydrates, small degraded nucleotides, host RNA, lipopolysaccharides, etc.

The expression "without effecting enzymatic digestion of RNA" refers to the absence of an enzyme such as RNase that digests RNA (including cellular or host RNA).

As used herein, "molecular weight cutoff" refers to the molecular weight of the globular solute that is 90% retained by that membrane. See Filtron Catalog, 1995/96, p. 5. The actual molecular weight of particles that pass through or are retained by a membrane will depend on the size as well as the conformation and charge of a given molecule, the nature of the membrane pore or matrix, and the conductivity and pH of the solution.

As used herein, a "purified" plasmid is one that is separated from contaminants such as endotoxin, protein, and RNA, and preferably composed of at least about 95% plasmid and about 5% RNA, more preferably at least about 98% plasmid and about 2% RNA, as measured by size-exclusion chromatography at 260 nm absorbance.

Preferably, the endotoxin levels in such purified plasmid preparation are less than 300,000 EU/ml, more preferably less than 30,000 EU/ml.

MODES FOR CARRYING OUT THE INVENTION

It has been found that plasmid DNA can be highly purified in large yields from prokaryotic cells in which it is contained using TFF but without RNase. Preferably, the plasmid DNA herein has a size ranging from about 2 Kb to 50 Kb, more preferably about 2 to 15 Kb, and the TFF uses a selective molecular weight cutoff of greater than about 500 kD, preferably from about 500 kD to 1000 kD.

Plasmid DNA herein is isolated, or extracted, from components of prokaryotic cell cultures, preferably bacterial fermentations, and most preferably *E. coli*. Plasmid DNA isolated from prokaryotic cells includes naturally-occurring plasmids as well as recombinant plasmids containing a gene of interest, including, e.g., marker genes or therapeutic genes. The fermentation may be carried out in any liquid medium that is suitable for growth of the cells being utilized.

The DNA plasmid to be purified herein may be any extrachromosomal DNA molecule of any character, provided that it is in the size range specified above. The plasmids may be high copy number, low copy number, or runaway plasmids, and may be single-stranded or double-stranded DNA, supercoiled plasmid DNA, or DNA fragments. They can contain a range of genetic elements that include selectable genes, polylinkers, origins of replication, promoters, enhancers, leader sequences, polyadenylation sites, and termination sequences. The plasmids can contain mammalian genes of basically any origin, preferably a therapeutic gene, and more preferably one encoding a human polypeptide of interest. Such therapeutic genes include functional genes or gene fragments that can be expressed in a suitable host to complement a defective or under-expressed gene in the host cell, as well as genes or gene fragments that, when expressed, inhibit or suppress the function of a gene in the host cell, including, e.g., antisense sequences, ribozymes, transdominant inhibitors, and the like.

Before digestion and lysis of the cells to extract the plasmid DNA, the cells are generally first harvested from the fermentation medium. Any conventional means to harvest cells from a liquid medium is suitable, including centrifugation, filtration, and sedimentation.

The first step of the process herein involves digesting the cells. Digestion may occur by any conventional procedure (e.g., by the technique of Birnboim and Doly, supra), but preferably is effected by adding a digesting enzyme such as lysozyme, mixing, and incubating the mixture at a temperature below room temperature, preferably on ice.

The second step of the process herein involves lysis and solubilization of the cells, which results in chemical digestion of the RNA. This step is carried out for a time that ranges from about 4 to 24 hours, preferably from about 6 to 24 hours, more preferably from about 10 to 24 hours, still more preferably from about 15 to 24 hours, and most preferably from about 20 to 24 hours. Typically, the cells are resuspended in buffer after harvest and treated for the indicated time period with one or more agents that function to lyse and solubilize the cells. Examples of such agents include alkali (e.g., dilute base such as sodium hydroxide) and/or a detergent. Preferably, both alkali and detergent are employed. In another preferred embodiment, for the maximum removal of endotoxin, the detergent is, for example, sodium dodecyl sulfate (SDS), cholic acid, deoxycholic acid, or TRITON X-114™, most preferably SDS or deoxycholic acid. For maximum plasmid release and removal of contaminating genomic DNA, the detergent is preferably anionic, more preferably SDS, cholic acid, or deoxycholic acid, and most preferably SDS or deoxycholic acid.

The lysing/solubilization step is conducted in the absence of enzymes that digest RNA such as RNase. Preferably, the process is also carried out in the absence of enzymatic treatment that would weaken any cell wall due to any possible animal viral contamination. It is also desirable to use methods that do not shear chromosomal DNA, so that its removal is facilitated and contamination with the final plasmid DNA product is avoided. The preferred lysis procedure for bacterial cells involves the alkaline lysis described in Birnboim and Doly, supra, or modifications thereof as reported in Example 1 herein.

After lysis and solubilization, the cells are treated to remove lysate contaminants, including cellular debris such as proteins, cell walls, or membranes, chromosomal DNA, and host proteins. This removal step typically involves precipitation, centrifugation, filtration, and/or sedimentation depending on the cell type and the type of lysis employed. If alkali lysis is utilized, preferably the resultant lysate is acidified to precipitate the chromosomal DNA and host proteins. Then cell debris and other impurities are preferably removed by standard means, such as centrifugation, filtration, or sedimentation, preferably centrifugation. The resultant supernatant is then optionally filtered with diatomaceous earth to clarify it and to reduce the concentration of host RNA with respect to the supernatant. The plasmid DNA can be precipitated from the clarified filtrate using a precipitating agent under suitable conditions, collected, and resuspended in a buffer. Subsequently, the host RNA, proteins, and lipopolysaccharides, as opposed to plasmid DNA, are preferably precipitated from the buffer with a precipitating agent under conditions appropriate for this purpose. Finally, the filtrate is preferably collected, the plasmid DNA re-precipitated using a precipitating agent under conditions suitable therefor, and the precipitated plasmid DNA re-suspended for use in the TFF filtration step.

The next step in the process involves filtering the solution through a TFF device. Prior to such filtering, the plasmid DNA may be treated with a short-chain polymeric alcohol, so that it does not bind to the TFF membrane as appropriate. A schematic diagram of a TFF process is shown in FIG. 1 of WO 98/05673. Sample apparatuses for carrying out HP-TFF are shown in FIGS. 2, 3, and 4 of U.S. Pat. No. 5,256,294. The filtration membrane is selected based on, e.g., the size and conformation of the plasmid DNA to be purified, and will have a molecular weight cut-off of greater than about 500 K daltons (kD), preferably about 500 to 1000 kD. Generally, the membranes useful for TFF herein are as described by Gabler, supra. They are typically synthetic membranes of either the microporous (MF) or the ultrafiltration (UF) type, with the reverse-osmosis (RO) type not normally applicable due to its small ranges of pore size.

An MF type has pore sizes typically from 0.1 to 10 micrometers, and can be made so that it retains all particles larger than the rated size. UF membranes have smaller pores and are characterized by the size of the globular protein that will be retained. They are available in increments from 1,000 to 1,000,000 nominal molecular weight (dalton) limits, corresponding approximately to 0.001 to 0.05 micrometers. UF membranes, which are normally asymmetrical with a thin film or skin on the upstream surface that is responsible for their separating power, are most commonly suitable for use in the present invention.

The process of the present invention is well adapted for use on a commercial or semi-commercial scale. It can be run semi-continuously, i.e., on a continuous-flow basis of solution containing the desired plasmid DNA, past a tangential flow filter, until an entire, large batch has thus been filtered, followed by a stage of continuous flow separation of contaminants from desired plasmid DNA. Washing stages can be interposed between the filtration stages. Then fresh batches of solution can be treated. In this way, a continuous, cyclic process can be conducted, to give large yields of desired product, in acceptably pure form, in relatively short periods of time.

Under these conditions, plasmid DNA will be retained in the retentate while the contaminating substances, including many proteins, cell membrane debris, carbohydrates, small degraded nucleotides, etc., pass through the membrane into the filtrate. Commercial sources for filtration devices include Pall-Filtron (Northborough, Mass.), Millipore (Bedford, Mass.), and Amicon (Danvers, Mass.). Any filtration device useful for conducting TFF is suitable herein, including, e.g., a flat plate device, spiral wound cartridge, hollow fiber, tubular or single sheet device, open-channel device, etc.

The surface area of the filtration membrane used will depend on the amount of plasmid DNA to be purified. The membrane may be of a low-binding material to minimize adsorptive losses and is preferably durable, cleanable, and chemically compatible with the buffers to be used. A number of suitable membranes are commercially available, including, e.g., cellulose acetate, polysulfone, polyethersulfone, and polyvinylidene difluoride. Preferably, the membrane material is polysulfone or polyethersulfone.

Filtration is performed using tangential flow to circulate the sample buffer as it crosses the membrane surface. During TFF, pressure is applied across the membrane, which will allow smaller molecules to pass through the membrane while the retentate is recirculated. Typically, the flow rate will be adjusted to maintain a constant transmembrane pressure. Generally, filtration will proceed faster with higher pressures and higher flow rates, but higher flow rates are likely to cause shearing of the nucleic acid or loss due to passage through the membrane. In addition, various TFF devices may have certain pressure limitations on their operation. The pressure, therefore, may be adjusted according to the manufacturer's specification. For flat-plate devices, the pressure is preferably about 5 to 30 psi, most preferably 10 to 15 psi. The circulation pump is selected to ensure minimal shearing of the nucleic acid. Typically, the circulation pump is a peristaltic pump or diaphragm pump in the feed channel and the pressure is controlled by adjusting the retentate valve.

Filtration will generally be performed in diafiltration mode. Optionally, the sample solution may initially be filtered without buffer addition until concentrated to a desired volume. Once concentrated, diafiltration buffer is added and filtration continues to wash the retentate of contaminating small molecules and remove unwanted solvents and salts. Diafiltration may be either continuous or discontinuous. Preferably, diafiltration is continuous, and performed until about 5 to 500 volume equivalents have been exchanged. Generally, more diafiltration will be performed with increased contaminants bound to the nucleic acids, depending on the purity required.

To further improve yield of the purified plasmid DNA following TFF, the retentate solution may optionally be recirculated through the filtration unit with the permeate valve closed for several minutes to remove residual plasmid DNA. The retentate is collected and additional diafiltration buffer is added to wash the membrane filter. The retentate is again collected and combined with the original retentate containing the purified plasmid DNA. The feed solution may then be concentrated and then dialyzed against a buffer such as TRIS™ to obtain purified plasmid DNA.

Plasmid DNA purified by the TFF process herein may be used directly or may be further purified depending on the level and type of contamination in the starting sample and the desired use. The plasmid DNA thus purified may be used for a number of applications, e.g., molecular biological applications such as cloning or gene expression, or for diagnostic applications using, e.g., PCR, RT-PCR, dendromer formation, etc. For therapeutic uses, e.g., for use in gene therapy or as a vaccine or in gene immunization, it may be desirable to further purify the plasmid DNA obtained from the TFF step. Ion-exchange chromatography may be used to further purify the plasmid DNA.

The plasmid DNA sample is loaded onto the column in a loading buffer comprising a salt concentration below the concentration at which the plasmid DNA would elute from the column. Typically, the salt concentration will be about 10 to 50mS, depending on the resin used. For weaker anion-exchange resins, a lower conductivity solution will be used, whereas for stronger anion-exchange resins, a higher conductivity solution will be used. The column will then be washed with several column volumes of buffer to remove those substances that bind weakly to the resin. Fractions are then eluted from the column using a shallow continuous saline gradient according to conventional methods, e.g., using up to 1.5M NaCl in a Tris-HCl buffer. Sample fractions are collected from the column. For intermediate-scale preparations (e.g., from about 100 mg to about 3 grams plasmid DNA), fractions will typically be at least 50 mL to 2 liters where the plasmid DNA peak is expected, then increased in volume past the expected peak. Analytical determinations of plasmid DNA yield and purity are performed on each fraction. In addition, Limulus ameobocyte lysate (LAL) analyses may be performed on each fraction to determine residual endotoxin levels in each fraction. Fractions containing high levels of plasmid DNA and low endotoxin are pooled.

Where plasmid DNA purified according to the above protocol is to be complexed with a lipid carrier for use in gene therapy, it is desirable to exchange the plasmid DNA into a low-conductivity buffer, preferably by diafiltration. A low-conductivity buffer is meant to include any buffer of less than about 10 mS, preferably less than about 1 mS.

At a variety of places in the above protocol, analytical determination of plasmid DNA yield and purity are advantageously performed. Typically, such assays are performed before and after each purification step, as well as to each nucleic acid-containing fraction from, e.g., preparative ion-exchange chromatography. Preferred means for performing these analytical determinations include high-performance liquid chromatography (HPLC) or size-exclusion chromatography (SEC) analysis of purity, spectrophotometric estimation of yield, silver staining and SDS-PAGE for protein analysis, and agarose gel electrophoresis and Southern blotting for DNA analysis.

The invention will be more fully understood by reference to the following examples. They should not, however, be construed as limiting the scope of the invention. All literature and patent citations mentioned herein are expressly incorporated by reference.

EXAMPLE 1

Materials and Methods

Generation of Factor VIII Cell Paste

For purification of factor VIII plasmid, *E. coli* that had been transformed with the gene for factor VIII (U.S. Pat. Nos. 5,618,788 and 5,633,150) was cultured in a 10-L fermentor and treated with cycloheximide to maximize production of plasmid DNA.

Transformation of *E. coli* and Overnight Fermentation

For purification of plasmid other than factor VIII, transformation-competent *E. coli* (DH5a) cells (Gibco-BRL) were transformed according to the manufacturer's protocol for the amplification of ampicillin-resistant ($Amp^R$) plasmids. Overnight cultures of colonies were grown in LB medium supplemented with carbenicillin (50 mg/mL).

Alkaline Lysis of *E. coli*

Alkaline lysis of *E. coil* was based on the procedure of Birnboim and Doly, supra, with modifications as indicated below. The *E. coli* cells were suspended in 8 mL of 50 mM glucose/25 mM Tris-HCl/10 mM EDTA (GTE), pH 8, per gram (wet weight) of cells. A total of 0.8 mL of a lysozyme solution (2 mg/mL in GTE) (Canadian Lysozyme Company, Abbotsford, British Columbia) was then added and, after mixing, the cells were incubated for 30 min. on ice. A total of 16 mL of a solution containing 0.2 mM NaOH and 1% SDS (or other detergent, as indicated) was added to the mixture per gram of cells and incubated overnight (or as indicated) at room temperature with slow, continuous stirring. A total of 12 mL of 5 M potassium acetate, pH 4.8, was added per g of cells and, after mixing, the mixture was placed in an ice bath. After 10 min. of incubation, the mixture was centrifuged at 13,000×g for 30 min. The supernatant was collected and clarified by pouring it through several layers of MIRACLOTH™ material (Calbiochem-Novabiochem Corporation, San Diego, Calif.).

Plasmid Purification Using TFF

The plasmid DNA, isolated from *E. coli* as described above, was purified in a TFF device (TFF membrane cassettes and cassette holders were from Pall Filtron Corporation, Northborough, Mass.) using 0.5 square feet of a polyethersulfone membrane per 10–15 g of cells processed. (This amount was typically observed after overnight shake culture.) The nominal molecular weight cutoff of the membrane was 500 or 1000 kDa. Feed rate into the TFF device was set at 0.5 liters/min/sq.ft. of membrane. Experiments indicated that the ultrafiltration membranes required 15–20 minutes of equilibration with the clarified supernatant under normal operating conditions prior to initiation of ultrafiltration to minimize initial yield losses in the filtrate. All experiments were conducted maintaining constant transmembrane pressure (TMP). In several experiments, it was determined that the preferred TMP was approximately 10–15 psi. Under these conditions, the filtration flux rate was approximately 1.5 liters/hour/sq.ft. membrane. For purification of the plasmid, the feed solution was concentrated two-fold and then dialyzed against 8–10 diavolumes of 20 mM Tris-HCl, pH 7.6.

Cesium Chloride Density Gradient Centrifugation

Isolation of plasmid using cesium chloride gradients was conducted as described in Clewell and Helinski, supra, and Miller, *Meth. Enzymol.*, 152: 145–170 (Berger and Kimmel, eds) (Academic Press: San Diego, Calif., 1987).

Size-Exclusion Assay

Samples were analyzed by injecting 100 µL onto a TSK-G5000PW™ column (7.5×300 mm) (Tosohaas, Montgomeryville, Pa.) that was equilibrated in 20 mM Tris-HCl, pH 7.5. The column was run at a flow rate of 1 ml/min. Column effluent was monitored by absorbance at 260 nm. Elution volumes for plasmid were compared to that of a standard isolated by the cesium chloride method.

Transfection of 293 Cells and Assay for Factor VIII Activity

The purified plasmids herein were transfected into 293 human embryonic kidney cells maintained on PS19 medium containing 10% heat-inactivated fetal bovine serum. Lipid/DNA transfection complexes were formed using lipofectin reagent (BRL, Gaithersburg, Md.) and 1 µg of plasmid DNA per complex as per the manufacturer's instructions. This mixture was then added to cells in 35-mm wells (6-well plates) followed by the addition of media. Twenty-four hours after transfection, media was harvested and assayed for Factor VIII by ELISA assay and for Factor VIII activity using the COATEST VIII:C/4™ kit (Chromogenix AB, Moelndal, Sweden) according to the manufacturer's instructions.

Protein Determination

Protein concentration was determined by the Bradford method (Bradford, *Anal. Biochem.*, 72: 248–254 (1976)) using bovine serum albumin as standard.

Results

Factors Affecting Plasmid Isolation and Purification

Several different types of anionic, cationic, and non-ionic detergents were analyzed for their ability to produce soluble plasmid after lysozyme digestion. Anionic detergents, as a class, were most effective at plasmid release. In addition, restriction enzyme digests with EcoRl (New England Biolabs, Beverly, Ma.) of the plasmid preparations resulting from anionic detergents did not indicate the presence of contaminating genomic DNA. Finally, anionic detergents were found, as a class, to produce solubilized plasmid preparations that were much lower in endotoxin (Table 1).

TABLE 1

The Effect of Different Detergents Used in Solubilization of Factor VIII Plasmid on Resulting Endotoxin Level

| Detergent | Endotoxin (EU/ml) | n |
| --- | --- | --- |
| Anionic: | | |
| SDS | 28,000 | 5 |
| cholic acid | 220,000 | 3 |
| deoxycholic acid | 18,000 | 2 |
| Non-ionic, zwitterionic: | | |
| TRITON X-100 ™ | 2,600,000 | 3 |
| TRITON X-114 ™ | 100,000 | 1 |
| TWEEN 20 ™ | 600,000 | 1 |
| TWEEN 80 ™ | 140,000 | 3 |
| BRIJ 35 ™ | 1,000,000 | 1 |
| NONIDET NP-40 ™ | 840,000 | 3 |
| W-1 ™ | 2,700,000 | 2 |
| ZWITTERGENT 3-14 ™ | 3,000,000 | 1 |
| Cationic: | | |
| benzylalkonium chloride | 2,500,000 | 2 |
| dodecyltrimethylammonium bromide | 1,300,000 | 2 |
| tetradecyltrimethyiammonium bromide | 1,000,000 | 1 |
| hexadecyltrimethylanrnonium bromide | 1,000,000 | 1 |

The effect of increasing the time of exposure to sodium hydroxide in the presence of two different anionic detergents was investigated. Increasing the incubation time resulted in an apparent time-dependent decrease in both the overall size and amount of the contaminating RNA. At 24 hours of incubation, little RNA was detectable in both the SDS-solubilized and cholate-solubilized preparations. Without being limited to any one theory, it is believed that, after extended exposure to alkaline conditions, contaminating RNA might be sufficiently degraded so as to allow purification of plasmid DNA from the RNA and other lower-molecular-weight contaminants (e.g., protein, endotoxin) by TFF. For maximization of the purification, the largest membrane pore size that still displayed retention of plasmid was selected. Both 500,000 and 1,000,000 Da nominal molecular weight cutoff membranes fulfilled this requirement. An initial experiment using plasmid exposed to sodium hydroxide and SDS for 4- and 24-hour time periods indicated that a 24-hour exposure was preferred for the removal of RNA by TFF.

Characterization of Purified Factor VIII Plasmid

Plasmid that had been isolated as described above, with either a 4- or 24-hour sodium hydroxide/SDS incubation followed by UF/DF purification, was comparable to plasmid that had been prepared using a standard CsCl gradient technique when compared on agarose gels. The amount of co-purifying RNA in the plasmid preparation was assessed using a size-exclusion chromatography assay. As shown in FIG. 1, greater than 99% of the contaminating RNA was removed by the filtration step. Protein concentration in the resulting TFF pools ranged from 10 to 30 ug/ml, which constitutes greater than 95% reduction of the total protein present in the potassium acetate supernatant. In five separate preparations, the yield of Factor VIII plasmid was 2.2±0.8 mg plasmid/g cells (wet weight). Endotoxin levels averaged 2400±1700 EU/ml (n=3).

Activity of Plasmid Purified by the TFF Method

Plasmid DNA containing the gene for Factor VIII was isolated by the TFF method and compared to the same plasmid, isolated by conventional CsCl procedures (Miller, supra) for the ability to transfect 293-HEK cells. As can be seen in Table 2, plasmid DNA isolated using the modified alkaline-lysis and TFF procedure herein had comparable activity to plasmid isolated using CsCl gradients.

TABLE 2

Comparison of Expression Levels with
TFF- and CsCl-purified Factor VIII Plasmid

| Plasmid | Factor VIII (ELISA) (mU/ml) | Factor VIII Activity (mU/ml) |
| --- | --- | --- |
| TFF-purified (4-hour NaOH incubation) | 4.0 | 11.1 |
| TFF-purified (24-hour NaOH incubation) | 3.8 | 9.9 |
| CsCl (fermentor) | 2.6 | 6.3 |
| CsCl (shake-flask) | 8.6 | 14.7 |

Application of the Procedure to Multiple Plasmids

The robustness of the TFF method was assessed by using the procedure with six different plasmids of varying size that had been transformed into *E. coli* and grown overnight in shake flasks. As is seen in Table 3, independent of the size of plasmid to be recovered, each preparation resulted in a minimum of 2 mg of purified plasmid DNA per g of cells (wet weight).

TABLE 3

TPF-Based Plasmid Isolation using Different Piasmids

| Plasmid size (kb) | Mass (kDa) | Recovery (mg plasmid) | Yield (mg plasmid/g of cell pellet) |
| --- | --- | --- | --- |
| 5.6 | 3,600 | 31 | 2.8 |
| 5.8 | 3,700 | 29 | 2.6 |
| 6.0 | 3,900 | 20 | 2.0 |
| 6.2 | 4,000 | 22 | 2.2 |
| 7.9 | 5,100 | 72 | 7.3 |
| 10.0 | 10,000 | not determined | 2.2 |

Conclusions

Described herein is a simple, scalable method for purification of large amounts of transfection-competent plasmid that is based on an extended (about 4–24-hour) lysis/solubilization step, followed by purification using a TFF step. This method yields 7–20 mg plasmid/liter of overnight culture, which is several-fold higher than values reported previously (Ishaq et al., supra; Kondo et al., supra; Chakrabarti et al., supra; Chandra et al., supra; Miller, supra). In addition, plasmid isolated using this procedure has been shown to have activity in a cell transfection assay comparable to plasmid isolated using classical methods.

The levels of endotoxin observed using the TFF method were higher than levels reported using alternative purification methods (Miller, supra). However, contrary to previous observations (Cotten et al., *Gene Ther.*, 1: 239–246 (1994); Weber et al., *Biotechniques*, 19: 930–940 (1995)), these levels of endotoxin did not adversely affect the ability of plasmid to transfect cells and express protein. Further, these levels of endotoxin can be substantially removed as necessary by further purification such as by ion-exchange chromatography.

The TFF-based purification procedure described herein is readily scalable using standard principles of TFF scale-up. Finally, the broad applicability of this procedure has been demonstrated by its effective implementation with several different plasmids of varied molecular weight.

What is claimed is:

1. A process for purifying plasmid DNA from prokaryotic cells comprised thereof, which process comprises the steps of:

(a) digesting the cells;

(b) incubating the cells in the presence of alkali and a detergent for about 4 to 24 hours to effect lysis and solubilization thereof;

(c) removing lysate contaminants from the cells to provide a plasmid DNA solution;

(d) filtering the solution through a tangential flow filtration device to obtain a retentate containing the plasmid DNA; and (e) collecting the retentate, whereby enzymes are not used in any of the above steps to digest RNA.

2. The process of claim 1 wherein the cells are bacterial cells.

3. The process of claim 1 wherein the cells are *E. coli* cells.

4. The process of claim 1 wherein the plasmid DNA has a size ranging from about 2 to 50 kilobases.

5. The process of claim 1 wherein step (a) is carried out using lysozyme.

6. The process of claim 1 wherein step (b) is carried out for about 10 to 24 hours.

7. The process of claim 1 wherein step (b) is carried out for about 20 to 24 hours.

8. The process of claim 1 wherein step (c) is carried out by centrifuging the lysate contaminants from the plasmid DNA to provide the plasmid DNA solution as a supernatant.

9. The process of claim 1 wherein the filtration device has a membrane with a molecular weight cutoff of greater than about 500 kD.

10. The process of claim 1 further comprising recovering the plasmid DNA from the retentate.

11. The process of claim 1 further comprising dialyzing the retentate against a buffer.

12. The process of claim 1 further comprising subjecting the retentate to ion-exchange chromatography.

13. The process of claim 1 wherein the detergent is ionic.

14. The process of claim 13 wherein the detergent is anionic.

15. The process of claim 14 wherein the detergent is sodium dodecyl sulfate, cholic acid, or deoxycholic acid.

\* \* \* \* \*